United States Patent [19]

Chan

[11] Patent Number: 4,618,585
[45] Date of Patent: Oct. 21, 1986

[54] HYBRIDOMA CELL LINES PRODUCING MONOCLONAL ANTIBODIES DIRECTED AGAINST CERVICAL CANCER CELLS

[75] Inventor: Teh-sheng Chan, League City, Tex.

[73] Assignee: Board of Regents, The University of Texas System, Austin, Tex.

[21] Appl. No.: 631,252

[22] Filed: Jul. 16, 1984

Related U.S. Application Data

[63] Continuation of Ser. No. 359,514, Mar. 18, 1982, abandoned.

[51] Int. Cl.[4] .................. C12N 5/00; A61K 39/395; C07K 15/00
[52] U.S. Cl. ............................. 435/240; 424/85; 530/387; 435/172.2
[58] Field of Search ............... 435/172.2, 240; 260/112 R, 112 B; 424/85

[56] References Cited

U.S. PATENT DOCUMENTS

| | | | |
|---|---|---|---|
| 4,172,124 | 10/1979 | Koprowski et al. | 424/85 |
| 4,196,265 | 4/1980 | Koprowski et al. | 435/2 |
| 4,271,145 | 6/1981 | Wands et al. | 424/85 |

OTHER PUBLICATIONS

Schlon et al., "Generation of Human Monoclonal Antibodies Reactive with Human Mammary Carcinoma Cells" *Proc. Natl. Acad. Sci. USA* 77:6841, (Nov. 1980).

Dippold et al., "Cell Surface Antigens of Human Malignant Melanoma: Definition of Six Antigenic Systems with Mouse Monoclonal Antibodies" *Proc. Natl. Acad. Sc: USA* 77:6114 (Oct. 1980).

Glass, David, "Medicine's Micro Missiles" *Science Digest*, pp. 30, 31, 114, (Jan. 1982).

Lakachura et al., "Monoclonal Antibodies Against Human Hela Cell Surface Antigens" Abstract of Tissue Culture Association (Mar. 20, 1981).

Wiels et al., "Monoclonal Antibody Against a Burkitt Lymphoma Associated Antigen", Proc. Natl. Acad. Sci. USA 78:6485, (Oct. 1981).

*Primary Examiner*—Blondel Hazel
*Attorney, Agent, or Firm*—Arnold, White & Durkee

[57] ABSTRACT

Continuous hybrid cell lines for producing monoclonal antibodies, the antibodies specific for an antigenic determinant unique to cervical cancer cells, have been developed. The hybrid cell lines were established by fusing differentiated lymphoid cells primed with intact human cervical cancer cells with myeloma cells, particularly plasmacytoma cells. The resulting fused hybrid cells were cultured in HAT tissue culture media which included a small concentration of deoxycytidine. Deoxycytidine was found to enhance the growth of the hybrid cells and subsequent yield of monoclonal antibodies secreted therefrom. Hybrid cell lines secreting monoclonal antibodies to antigenic determinants unique for human cervical cancer cells can be maintained indefinitely in culture to produce large amounts of homogenous anti-cervical cancer cell antibody.

2 Claims, No Drawings

HYBRIDOMA CELL LINES PRODUCING MONOCLONAL ANTIBODIES DIRECTED AGAINST CERVICAL CANCER CELLS

The Government has rights in the invention pursuant to National Institutes of Health Grant No. 5 RO1 GM26522 awarded by Department of Health, Education and Welfare.

This is a continuation of application, Ser. No. 359,514 filed Mar. 18, 1982, now abandoned.

BACKGROUND OF THE INVENTION

The present invention relates to the production of monoclonal antibodies; and, in particular, to hybrid cell lines capable of continuously producing monoclonal antibodies directed against the antigenic determinants unique to cervical cancer cells. The present invention further relates to tissue culture media for enhanced growth of hybrid cell lines.

In recent years, the capability to produce monoclonal antibodies specific for the antigenic and immunogenic determinants of cell surface antigens has provided a new vista of diagnostic and immunotherapeutic agents.

For example, monoclonal antibodies have been available for some time now which are specific for an assortment of antigens, including viral antigens, such as rabies, hepatitis and influenza virus; red blood cells; fluorescent dyes; and cell associated antigens including human tumors such as melanoma, colorectal cancer, glioma, choriocarcinoma, renal cancer, breast cancer, lymphoma, and leukemia. Heretofore, as far as applicant is aware, there have been no reports of the production of continuous cell lines of somatic cell hybrids which elaborate monoclonal antibodies to antigenic determinants of cervical cancer cells, in particular cell surface exposed antigenic determinants.

The recent development of lymphocyte hybridoma technology has made possible the production of monoclonal antibodies specific for any given antigen. The production of a concentrated and homogenous source of antibodies specific for a singular antigenic determinant is of significant importance as analytical, diagnostic and immunotherapeutic tools.

It is therefore highly desirable to provide a means for producing a concentrated and homogenous source of antibody directed against antigenic determinants unique to cervical cancer cells. Such antibodies are important in the diagnosis of cervical cancer, in the purification of specific immunogens for subsequent medical research and potential development of vaccines, and in use as highly specific immunotherapeutic agents to direct cytotoxic agents to tumor cells.

SUMMARY OF THE INVENTION

In accordance with the present invention, continuous hybridoma cell lines are established which elaborate and secrete highly specific and homogenous monoclonal antibodies to antigenic determinants unique to cervical cancer cells. Further in accordance with this invention a hybridoma culture media is provided which has incorporated therein the compound deoxycytidine. Incorporation of deoxycytidine to the culture media significantly enhances the viability of cultured hybridoma cells and consequently enhances the yields of monoclonal antibodies secreted therefrom.

In its broadest aspect, the invention involves first immunizing an animal to cervical cancer cells to develop lymphocytes and their differentiated progeny primed to produce antibodies directed against a specific priming antigenic determinant. The lymphocytes are recovered and fused with myeloma, plasmacytoma, or hybridoma cells to form somatic cell hybrids (hybridoma). The cell hybridomas are cultured, selected, and propagated in tissue culture. To enhance viability of a selected hybridoma cell line, a small concentration of deoxycytidine, 2'-deoxyribocytosine, is added to the tissue culture media. Thereafter, the selected hybrid cell line is capable of indefinitely producing a high yield of monoclonal antibodies to a specific priming antigen expressed by cervical cancer cells.

The monoclonal antibodies are separated and recovered from the hybrid cell line and culture medium for subsequent use as an immunosorbent analytical agent in the detection of cervical cancer cells.

DETAILED DESCRIPTION OF PREFERRED EMBODIMENTS

The following discussion is in terms of the preferred embodiments of this invention, which represent the best mode known to the applicant at the time of this application.

In accordance with the processes of this invention, test animals are primed for antibody production by immunization with a preparation containing antigenic components of human cervical cancer cells. For example, the immunizing agent is suitably substantially intact human cervical cancer cells, a heterogenous composition of disrupted cervical cancer cells or a cell membrane fraction of cervical cancer cells. Applicant has directed his preferred embodiment to immunizing mice with intact human cervical cancer cells.

Alternative to immunizing a test animal, normal and immune differentiated lymphocytes capable of producing antibody isolated from test animals can be primed in vitro. For example, such in vitro stiumulation methods with mitogens and/or antigens have been described by Robertson et al, *Microbiology* 1980 pp. 181–185 (1980) and Kettman et al, *J. Immunolo. Methods* 39:203–222 (1980) or the method splenic fragment culture as described by Press et al, *Eur. J. Immunol.* 4:155–159 (1974).

The route and schedule of immunization of the test animal or cultured antibody producing cells are generally in keeping with established and conventional techniques for antibody stimulation and production. Applicant has employed mice as the test model, although it is contemplated that any mammalian subject, including human subjects, or antibody producing cells derived therefrom can be manipulated according to the processes of this invention to serve as the basis for obtaining primed antibody producing cells.

After immunization, the antibody producing cells, preferably immune lymphoid cells, are fused with myeloma, plasmacytoma, or hybridoma cells (hereinafter referred to collectively as myeloma cells) to generate a hybrid cell line which can be cultivated and subcultivated indefinitely, and which produce large quantities of monoclonal antibodies. For purposes of this invention, the immune lymphoid cells selected for fusion are desirably lymphocytes and their normal differentiated progeny, taken either from lymph node tissue or spleen tissue of immunized animals. Applicant prefers to employ immune spleen cells, since they offer a more concentrated and convenient source of antibody producing cells with respect to the mouse system.

The myeloma cells provide the genetic basis for continuous propagation of the resultant fused hybrid. Myeloma cells are tumor cells derived from plasma cells which show preference for bone marrow. Generally, myeloma cells are antibody producing cells although the specificity of the antibody is unknown. It is possible however to employ myeloma cells which are devoid of inherent antibody synthesis activity. Applicant prefers to use plasmacytoma cells as the fusing myeloma cell.

The particular species of animal from which the myeloma and primed antibody producing cells are derived are not critical, in that it is possible to fuse cells of one species with another. However, it is preferred that the source of primed antibody producing cells and myeloma be from the same species. Moreover, if the antibody producing cells and myeloma cells are derived from the same species strain the derived fused hybridoma will be isogenic with respect to the strain. Later, when the selected isogenic hybridoma is propagated it may be cultured in vivo in the form of ascites or a solid tumor as well as cultured in vitro in conducive tissue culture media.

Generally the fusion techniques employed are according to the procedures set out by Kohler et al, *Eur. J. Immunol.* 6:11-19 (1976) and Kennett et al, *Lymphocyte Hybridomas—Current Topics in Microbiology and Immunology* 81:77-91 (1978) Springer-Verlag, New York. Fusion is generally accomplished by adding a suspension of the primed antibody producing cells to the myeloma cells in growth medium and centrifuging to form a pellet.

The fused hybrids are next screened for antibody production specific for antigens unique to cervical cancer cells. Applicant has determined that inclusion of a small concentration of deoxycytidine into the hybridoma tissue culture medium media will enhance the viability of the hybridoma and subsequent antibody yield as compared to hybridoma grown on conventional HAT medium. The monoclonal antibodies obtained according to preferred examples exhibit individual specificity for one of the numerous antigenic components expressed by cervical cancer cells and particularly cell surface antigens, including lipopolysaccharides, lipids, and protein antigenic determinants.

The hybridomas which secrete antibody specific for and selective to antigens of cervical cancer cells are cultured to establish a continuous cell line with stable genetic coding. These cell lines can be stored and preserved in any of a number of conventional ways, including freezing and storage under liquid nitrogen. Frozen cell lines can be revived and cultured indefinitely with resumed synthesis and secretion of monoclonal antibodies specific for the primed antigenic determinant of cervical cancer cells. The secreted monoclonal antibody is recovered from the tissue culture supernatant by conventional methods, such as precipitation, ion exchange, affinity chromatography, or the like. The recovered antibody can be freeze dried and stored under refrigeration for at least several weeks without significant loss of activity.

The following examples are offered to illustrate a particular embodiment of the invention but they are not intended to limit it.

THE IMMUNIZING CELLS

The immunizing cells used to prime a Balb/c mouse test system were HeLa cells isolated by Gey et al from a carcinoma of the cervix (*Cancer Research* 12:264 (1952)) obtained through the American Type Culture Collection (CCL-2) in Rockville, Md. The cells are an epithelioid cell line which share many antigenic determinants in common with other human cells, either epithlial or non-epithelial in origin. Generally, antibody producing cells primed with the HeLa cancer cells will express antibodies that cross react with antigenic determinants from normal, noncancerous cervical cells. However, there are antigenic determinants on HeLa cancer cells which are unique to HeLa and not expressed by normal cervical cells. These unique determinants are the focal determinants to which the present invention envisions as the source for priming monoclonal antibody specificity.

B. HYBRIDOMA PREPARATION

Balb/c mice were injected intraperitoneally with $10^7$ human cervical cancer cells (HeLa) four times at weekly intervals. Four days after the last injection, the spleen was dissected from the mouse. Next the spleen was needle punched to facilitate removal of single cells to be suspended in 20 ml Dulbecco and Vogt medium with high glucose 4.5 g/L and 10% fetal calf serum (DV-10).

The suspended spleen cells were centrifuged at 600 xg for 5 minutes and the supernatant medium removed. The residue pellet was gently resuspended in 5 ml cold 0.17M ammonium chloride. The resulting suspension was incubated in an ice bath for eight minutes to lyse the erythrocytes. The remaining intact cells were centrifuged for five minutes at 600 xg, the medium decanted and the pellet resuspended in 5 ml DV-10.

Approximately $1-2 \times 10^8$ spleen cells were then mixed with $1-2 \times 10^7$ plasmacytoma cells (P3×63Ag8) (Kohler and Milstein, *Nature* 256: 495-497 (1975)) in a round bottom centrifuge tube. These cells were then washed with serum free (DVO) medium. Supernatant medium was removed by suction and the remaining pellet was loosened by tapping the tube. To this was added 0.5 ml of warm (37° C.) 50% polyethylene glycol-1000 (PEG) (in serum free (DVO) medium) dropwise with gentle mixing. After 5 minutes incubation at room temperature, the suspension was centrifuged at 250 xg for 5 minutes. PEG was carefully removed by a pasteur pipet, and 5 ml of serum free (DVO) medium was slowly added to the pellet. This was followed by slow addition of 5 ml DV-10. The suspension was centrifuged and pellet was resuspended in 30 ml of hybridoma medium. Hybridoma medium consisted of Dulbecco and Vogt medium with high glucose 4.5 g/L, supplemented with 20% fetal calf serum, $1 \times 10^{-4}$M hypoxanthine, $1.8 \times 10^{-5}$M thymidine, $2 \times 10^{-6}$M deoxycytidine, (obtained from Sigma Chemical Co.), and $3.4 \times 10^{-3}$M glutamine. The cells were evenly suspended and gently distributed in six microtiter plates (Costar, 96 well tissue culture clusters). Plates were incubated overnight in $CO_2$ incubator at 37° C. The next day an additional drop of hybridoma medium containing $1.6 \times 10^{-6}$M aminopterin was added to each well. Final concentration of aminopterin per well was $8 \times 10^{-7}$M.

Plates were placed in a moist chamber which was then placed in the incubator. One week later wells were fed with 1 drop (50 ul) of hybridoma medium. On day 17, wells containing growing clones were screened for antibody production by an enzyme linked immunosorbent assay. Positive clones were identified and expended by stepwise transfer to larger wells and finally to flasks. Cells were frozen in liquid nitrogen.

C. IDENTIFICATION OF HYBRIDOMAS SECRETING ANTIBODY SPECIFIC FOR HELA ANTIGENS $5 \times 10^4$ HeLa cells were plated in each well of a microtiter plate. The next day the media was removed and monolayers were washed twice with phosphate buffered saline (PBS). To each well was then added 50 ul of 0.2% cold glutaraldehyde and plates were incubated 15 minutes at room temperature. Free glutaraldehyde was washed from monolayers and residual glutaraldehyde was blocked by 100 mM glycine in 0.1% bovine serum albumin solution by incubating plates for 30 minutes in the above solution. After washing the fixed cell monolayers twice with PBS, 50 ul medium from hybridoma wells was added to each well. Cells were incubated with test medium for 2 hours at room temperature. These cells were then washed 3 times with PBS followed by addition of 100 ul/well of peroxidase labelled anti-mouse Ig (1:1000, Miles Laboratories). Incubation was carried out for 2 hours at room temperature and then the plates were washed six times with PBS. Substrate solution was prepared by dissolving orthophenyldiamine in 0.1M citrate buffer pH 4.5 at a concentration of 1 mg/ml and hydrogen peroxide (30%) 0.4 ul/ml. Two hundred ul of above substrate solution was added to each well and the reaction was followed for ½ hour. Positive-negative selection was made visually.

For quantitative determination of antibodies having specificity for HeLa cells, a modified enzyme linked immunosorbent assay was performed, in which the enzyme used was beta-galactosidase and the substrate was nitrophenyl galactoside. After an incubation period of two hours, reactions were quantitated by measuring the absorbance at 410 nm.

D. CHARACTERISTICS OF HYBRIDOMAS SECRETING ANTIBODY SPECIFIC FOR HELA CELL ANTIGENS

Of approximately two hundred clones derived from three separate experiments, thirty four reacted strongly with cells. These clones were further analyzed against a panel of five different human cell lines: WI38, WISH (from American Type Culture Collection), GM 3322 (a T-cell leukemia line) and GM 1897 (a B-cell leukemia line, both from Human Genetic Mutant Cell Line Repository). The antibody produced by clone designated as 2C1 reacted with all four test cell lines, indicating that the antibody has a broad specificity. In contrast, clones termed 1A3, 2B1 and 2B2 produced antibodies that reacted only with HeLa cells. The product of clone 1D3 is also of interest because it reacted with HeLa and WISH, both of which are epithelial cell lines, but not with T- and B-cell leukemia lines.

The majority of clones belong to the group represented by clone 2C1, that is, having broad specificity. Only 1% of isolates (Clones 1A3, 2B1, and 2B2) exhibited the unique characteristics of secreting antibodies specific for and selective to HeLa cells. Clone 1A3 has been deposited with the American Type Culture Collection and designated HB8563.

E. UTILITY

The hybridoma cell lines and the monoclonal antibodies produced therefrom having specificity for HeLa antigens described in this application are useful for medical and immuno-chemical research which may ultimately lead to the identification of antigens associated with human cervical cancer cells as distinguished from antigens expressed by normal cervical cells. Furthermore, diagnostic methods are envisioned wherein the monoclonal antibodies of this invention are tagged with a radioactive or fluorescent tracer for the in vitro detection of cervical cancer from biopsy samples. Moreover, the monoclonal antibodies of this invention can be utilized in immunotherapeutic techniques involving the specific and selective destruction of cancer cells in vivo. For example, the antibodies in conjunction with cytotoxic agents provide a vehicle to target the cytotoxic compounds to cancer cells in patients. In another application, the monoclonal clonal antibodies are useful as affinity binding agents for the extraction and purification of cervical cancer associated antigens.

While the invention has been described in terms of the preferred embodiments constituting the best mode known to the applicant at the time of this application, various changes may be made in the invention without departing from the scope thereof, which is defined by the following claims.

What is claimed is:

1. A continuous hybrid cell line having ATCC deposit number HB8563 and clones thereof, which cell line produces monoclonal antibody to an antigenic determinant unique to HeLa cervical cancer cells.

2. Monoclonal antibodies to an antigenic determinant unique to HeLa cervical cancer cells, the monoclonal antibodies produced from hybrid cell line ATCC deposit HB8563 and clones thereof.

* * * * *